United States Patent [19]

Polis et al.

[11] 4,153,808

[45] May 8, 1979

[54] NOVEL PROSTAGLANDIN DERIVATIVES, CERTAIN IN VIVO AND IN VITRO EFFECTS THEREOF AND PROCESSES FOR THE PREPARATION OF SAME

[76] Inventors: B. David Polis; Edith Polis, both of 8519 Patten Rd., Wyndmoor, Pa. 19118

[21] Appl. No.: 635,947

[22] Filed: Nov. 28, 1975

Related U.S. Application Data

[63] Continuation of Ser. No. 429,306, Dec. 28, 1973, abandoned.

[51] Int. Cl.$^2$ ............................................ C07C 177/00
[52] U.S. Cl. ...................................... 562/503; 424/317
[58] Field of Search ...................... 260/468 D, 514 D

*Primary Examiner*—Robert Gerstl
*Attorney, Agent, or Firm*—R. S. Sciascia; Henry Hansen; Norman H. Stepno

[57] ABSTRACT

The novel prostaglandins $PGB_x$ are useful for a wide variety of in vivo and in vitro biological properties, including the reversal of degenerative changes in mitochondria, the protection of the heart against cardiac insults, the protection and reversal of anoxic damage to the brain, and the improvement of mammalian performance for conditioned psychological tasks. These prostaglandins $PGB_x$ are prepared, for example, by the base catalyzed reaction of $PGB_1$.

12 Claims, 11 Drawing Figures

G = 2

A     B     C     D

A- Partially Purified Mixture
B- Slow Moving Active Component
C- Fast Moving Active Component
D- Inactive Component

NOVEL PROSTAGLANDIN DERIVATIVES, CERTAIN IN VIVO AND IN VITRO EFFECTS THEREOF AND PROCESSES FOR THE PREPARATION OF SAME

This is a continuation of application Ser. No. 429,306 filed Dec. 28, 1973 now abandoned.

BACKGROUND OF THE INVENTION

1. Field of the Invention

This invention relates to novel prostaglandin derivatives, and, more especially, to the novel prostaglandin derivatives, herein deemed the prostaglandins $PGB_x$, which are distinguishingly characterized by such exemplary in vitro and in vivo biological properties as: [1] dramatic effects on mitochondria of mammalian organisms, e.g., their ability to restore oxidative phosphorylation in degenerated mitochondria that have lost this function; [2] their protection and probable reversal of anoxic damage to mammalian brain; [3] their reversal of degenerative changes (coronary infarct) in heart; and [4] their improvement of mammalian performance for conditioned psychological tasks. The invention also relates to certain processes for the preparation of the topic prostaglandins $PGB_x$, for example, by the base catalyzed reaction of $PGB_1$; to the resolution of the reaction products into various components; and to the purification of such components into fractions exhibiting varying degrees of the aforesaid activities.

2. Description of the State of the Art

Previous studies on humans subjected to physical or psychic stress revealed common plasma increments in the level of phosphatidyl glycerol. Similar changes were found in the plasma and tissues of acceleration-stressed rats. The effects of acceleration on the plasma level of phosphatidyl glycerol could be reproduced by the injection of prostaglandin $E_1$. In vivo experiments showed exceptionally fast turnover rates of $P^{32}$ in phosphatidyl glycerol isolated from liver mitochondria of rats. These observations led to studies on the possible role of prostaglandins and phosphatidyl glycerol in phosphorylation mechanisms. When aged mitochondria were further "uncoupled" with Triton X-100 and reacted with adenosine diphosphate and $P^{32}$ under conditions for oxidative phosphorylation, analysis of the reaction products by ion exchange chromatography gave increased levels of adenylic acid and inorganic phosphate. Addition of prostaglandin $E_1$ and phosphatidyl glycerol to the reaction reversed the dephosphorylation and yielded a net increase in adenosine triphosphate correlated with a decrease in inorganic phosphate. In the presence of Triton X-100, both prostaglandin $E_1$ and the prostaglandin $B_x$ according to the invention were equally effective in reactivating phosphorylation. In the absence of Triton X-100, prostaglandin $E_1$ was inactive but prostaglandin $B_x$ was effective alone. Thin layer chromatography on silica of the one minute reaction products extracted by chloroform-methanol separated a radioactive phosphate labelled lipid component derived presumptively from prostaglandin $B_x$. This implication of prostaglandin $B_x$ as a possible intermediate in mitochondrial phosphorylation offered a new probe to the mechanisms involved in the transformation of oxidative energy. Compare Polis, B.D., A. M. Pakoskey, and H. W. Shmukler, "Regeneration of Oxidative Phosphorylation In Aged Mitochondria By Prostaglandin $B_1$", Proc. Nat. Acad. Sci., 63:229 (1969).

Further, the injection of various of the prostaglandins ($PGE_1$, $PGF_1$, $PGB_1$ and the $PGB_x$ prostaglandins according to the invention) into rats caused changes in plasma and brain phosphatidyl glycerol and related phospholipids that mimic the changes found in accelerated rats and in the plasma of physically or psychically stressed humans. The prostaglandin effects on normal rat plasma phospholipids were abolished in the hypophysectomized rat. A similar block in phospholipid change was observed in hypophysectomized rats subjected to acceleration stress. All of the above prostaglandins caused significant increases in plasma and brain phosphatidyl glycerol. Differences were observed in the effects on other phospholipids. Thus, $PGE_1$ decreased the total plasma phospholipid and phosphatidyl choline levels, while $PGF_1$ increased both levels. $PGE_1$ caused severe symptoms of lassitude and diarrhea in both normal and hypophysectomized rats. These effects were absent with the other prostaglandins. In contrast, the $PGB_x$ of the invention appeared to enhance the state of well being and lively behavior of the rat. These results, in conjunction with other previous work[1] on phospholipids in stress, implicate the prostaglandins in an adaptive response to stress which involves the mobilization of energy yielding molecular components and a gearing of metabolic events for survival. See Polis et al., "Prostaglandin Induced, Stress Related, Phospholipid Changes In The Rat", Bureau of Medicine and Surgery, Work Unit No. MR005.06.01-0011B, Report No. 3, Aerospace Medical Research Department, NADC-MR-7006 (10 June 1970), NTIS Accession Document 708379, hereby expressly incorporated by reference.

[1] Polis et al., "Effect Of Physical And Psychic Stress On Phosphatidyl Glycerol And Related Phospholipids", Biochem. Med., 2(4):286 (1969).

Moreover, on the simplistic premise that an anoxic-fatigue stress, like acceleration, could be defined in terms of energy demand under conditions of limited supply, a search has been reported for molecular probes which would reveal or reflect those regulatory mechanisms pertinent to the bioenergetic pathways involved in adaptation to stress. According to such search, it was expected that the exhaustion of adaptive events, and the onset of pathology, would be presignaled by molecular changes which might afford a biochemical index or end point to stress tolerance. It was additionally thought that such information would be useful also to amortize, pharmacologically, the energetic cost of a defensive reorganization against stress, and thereby enhance the survival of a crisis period. Compare Polis et al., "Some In Vitro And In Vivo Effects Of A New Prostaglandin Derivative" Advances Exp. Med. Biol., 33, 213 (1972), hereby expressly incorporated by reference and relied upon, and wherein it is indicated:

Experiments with isolated particulate fractions from animal cells revealed marked changes in a specific phospholipid identified as phosphatidyl glycerol (G) that followed exposure to an acute stress like acceleration or a longer termed degenerative stress like X-irradiation. These stress induced changes in the phospholipid composition of tissues and their correlation with comparable changes in plasma phospholipds of the rat suggested an approach to stress induced chemical changes in humans.

The effects of both physical and psychic stress on human plasma phospholipids are shown in FIG. 11 infra. These are portrayed as three dimensional plots of the means±two standard errors for G, phosphatidic acid (P) and phosphatidyl ethanolamine (PE). It is evident that in all the populations exposed to the various stresses of acceleration, sleep deprivation, combat flying, or the stress accompanying schizophrenia, there was a significant increase in G over the controls. Variations in other phospholipids made possible the statistical discrimination of stressed populations from each other.

In all the stress reactions studied, G was unique in the consistently elevated plasma levels which were common to all the stresses. In contrast, other phospholipids showed variable changes which facilitated a molecular characterization of the stress. These concentration shifts in individual phospholipids were not a direct consequence of variations in the total phospholipid content. Both increments and decrements of specific phospholipids were observed with no changes or even opposing changes in the levels of the total phospholipid content. Whether this represented a concentration effect in the output of a major regulatory factor or whether each phospholipid was uniquely controlled, the results implied the action of some brain centers which interpreted sensory inputs as "threats to survival" and in reacting, mobilized the phospholipids. That this hypothesis had some merit was indicated by the release of G from the brains of stressed humans.

Also shown were the results of collaborative studies on the differences in G between jugular venous and femoral arterial blood plasma from subjects under control conditions and after acceleration to grayout. It is apparent that there is indeed a significant release of G from the brains of the subjects after acceleration. The singularity of G is emphasized by the failure of all other phospholipid species to show any significant concentration change across the human brain after grayout.

Some indications of triggering factors for the phospholipid changes in stress can be obtained from the fact that the injection of various prostaglandins into rats caused major changes in G and lesser changes in other phospholipids that mimic the results obtained in stressed rats and humans. The increases in plasma G in the rat were accompanied by elevations of brain G. Although all four of the prostaglandins shown in FIG. 1, including the prostaglandins $PGB_x$ according to the invention, caused elevations of plasma G, they differed in their effects on other phospholipids. Prostaglandin $E_1$ ($PGE_1$) caused a significant decrease in lecithin (Le) and total phospholipid while Prostaglandin $F_{1\alpha}$ ($PGF_{1\alpha}$) caused an increase in Le and total phospholipid. The changes in total phospholipid were nonsignificant for $PGB_1$ and the topic $PGB_x$ and the variation in Le less marked. Variable effects on the concentration changes of P were observed with the different prostaglandins. The greatest change was obtained with $PGE_1$. There also were marked differences in observable physiological response. $PGE_1$ injection was followed by severe lassitude and diarrhea so that the rats appeared visibly ill. This response was absent with the other prostaglandins. With the subject $PGB_x$, the rats even appeared more lively and excitable.

SUMMARY OF THE INVENTION

Accordingly, a primary object of this invention is the provision of the novel prostaglandin derivatives $PGB_x$ which displayed the most dramatic in vitro effects on mitochondria.

Another object of this invention is the provision of a process for the preparation of such novel prostaglandins $PGB_x$.

Still another object of the invention is the preparation of the novel prostaglandins $PGB_x$ by the base catalyzed reaction of $PGB_1$.

Other objects, features and advantages of the invention, including certain additional in vitro and in vivo effects of the prostaglandins $PGB_x$, and comprising certain regenerative and/or protective effects on heart and brain tissue, will become apparent to those skilled in the art from the description which follows.

DETAILED DESCRIPTION OF THE INVENTION

Figure 1:
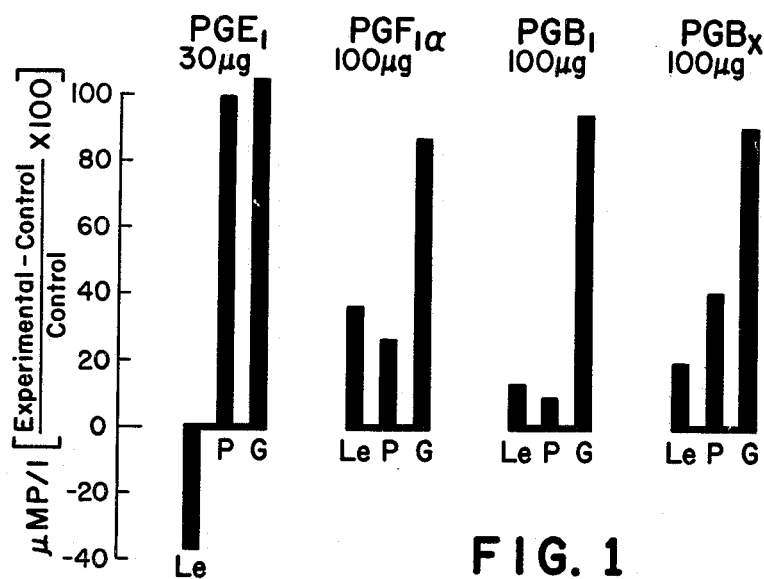
FIG. 1 is a graph of variation in phospholipid effects correlated with structural changes in prostaglandins.

The cyclopentanone ring of $PGE_1$ has a hydroxyl group $\beta$ to a keto group. Dehydration in dilute alkali then readily occurs and with rearrangement of the double bond $PGB_1$ is formed. These changes are followed by the appearance of an absorption band at 278 nm. When the NaOH concentration is raised to 1 molar in 50% alcohol and the prostaglandin is heated at 65° C., the 278 band disappears and two bands at 247 and 370 appear. These components react further to give a mixture that contains the active component $PGB_x$ of the invention and shows no well defined peak in the UV. When the base catalyzed reaction products are acidified and extracted into ether they can be resolved by thin layer chromatography into components which are distinguished by their fluorescence under long wave UV as well as by their mobilities. Purification of $PGB_x$ by elution of the orange band resolved by thin layer chromatography or in larger quantities by column chromatography on PVP eluted with heptane-alcohol gradients yielded the active component which had as an essential part of its structure as enolized $\beta$-diketone.

Using Warburg techniques for measuring oxygen uptake and hexokinase with glucose as a phosphate trap, mitochondria, aged for 4 to 5 days shows little or no phosphate esterification and comparatively low oxygen uptake with $\alpha$-ketoglutarate and ADP or AMP as substrate even in the presence of serum albumin. With the addition of 0.1 micromole $PGB_x$ to the reaction, there was a marked recovery of both phosphorylation and oxygen uptake. Even with AMP as phosphate acceptor the $PGB_x$ channeled the reactions from dephosphorylation to phosphorylation with changes in P/O ratios from 0 to 1.5, as is shown in the following Table I:

Table I

Effect of $PGB_x$ on Phosphorylation Efficiency of Aged Mitochondria

| Age (days) | Substrate | p esterified | O uptake | P/O |
|---|---|---|---|---|
| 4 | control ADP | 0.07 ± 0.8 | 2.1 ± 0.36 | 0.03 |
|  | $PGB_x$ | 8.92 ± 0.45 | 8.0 ± 0.26 | 1.12 |
| 5 | control AMP | −0.1 ± 0.01 | 0.8 ± 0.04 | — |
|  | $PGB_x$ | 5.8 ± 0.04 | 3.8 ± 0.20 | 1.53 |

To prove that the $PGB_x$ of the invention actually reactivated the net synthesis of ATP, mitochondrial reactions were run using ADP as the acceptor for phosphate. The changes in the nucleotide composition were measured by chromatography of the deproteinized reaction on a pellicular ion exchange column. This procedure[2] can quantitatively separate mixtures of AMP, ADP nd ATP in 10μ liter samples with a sensitivity in the order of 0.1 nanomole of nucleotide. The net disappearance of inorganic phosphate was measured separately by colorimetry.
[2]Shmukler, Herman W., J. Chromatog. Sci., 8, 653 (1970).

The data summarized in the following Table II show the nucleotide distribution in the reactions. At zero time the reaction mixture contained essentially inorganic phosphate and ADP plus a small amount of AMP formed by the splitting of ADP. In the control reaction run for 20 min. there was actually an increase in Pi because of ATPase and ATP by the adenylate kinase present. With the addition of $PGB_x$ to the reaction mixture there was clearly a shift to phosphorylation with a net synthesis of ATP corresponding to the decrease in inorganic phosphate.

Table II

Nucleotide Distribution and $P_i$ esterified in Control and $PGB_x$ Activated Mitochondrial Reactions for Oxidative Phosphorylation

| Reacton | μ Moles | | | |
|---|---|---|---|---|
|  | AMP | ADP | ATP | $P_i$ esterified |
| O Time Control | 0.22 | 4.55 | <0.01 | 0 |
| (20min.) | 1.76 | 1.41 | 0.75 | −0.53 |
| $PGB_x$ (20min.) | 0.07 | 0.57 | 4.00 | 4.74 |

Figure 2:
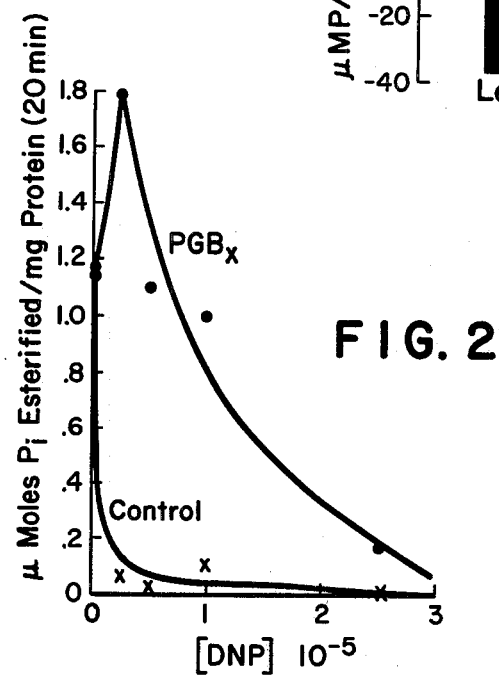
FIG. 2 is a graph of the effect of $PGB_x$ on DNP inhibition of 24 hour mitochondria.

The $PGB_x$ activation of oxidative phosphorylation was blocked by conventional inhibitors like oligomycin, dinitrophenol, dicumerol or pentrobarbitol but with interesting concentration effects. At low levels of the inhibitor, a potentiation of the prostaglandin activation was observed. With increased concentrations of the inhibitor the effect was diminished and finally completely blocked, see FIG. 2.

Figure 3:
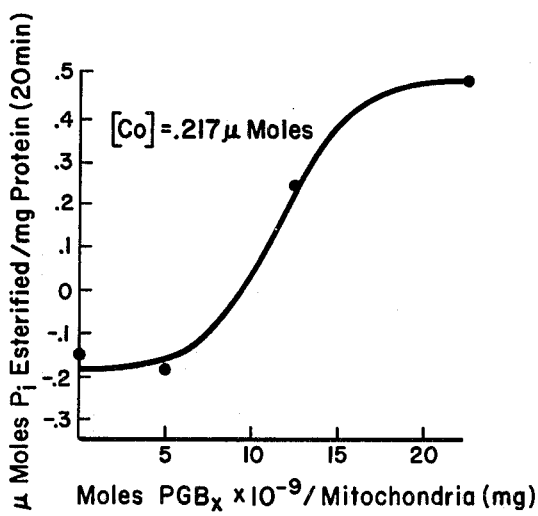
FIG. 3 is a graph of calcium inhibition of mitochondrial phosphorylation by $PGB_x$.

Of the inhibitors of oxidative phosphorylation studied possibly the most important from the standpoint of its implications to stress was the interplay between Ca++ and $PGB_x$ to control mitochondrial phosphorylation. Recently the uptake of CA++ in preference to phosphorylation has been detailed from a number of laboratories, especially those of Chance and of Lehninger[3,4]. FIG. 3 illustrates the activation curve for $PGB_x$ in a mitochondrial system inhibited with Ca++. In aged preparations the addition of CA++ at low levels enhanced dephosphorylation. This increase in inorganic $PO_4$ was blocked as the Ca++ was increased (4x) with no net phosphorylation. With the addition of $PGB_x$, there was an activation of phosphorylation and a cancellation of the Ca++ effect over the Ca++ range studied. Thus, in the competition between Ca++ and $PGB_x$ for the direction of oxidative energy, an in vitro mechanism is available for the control of phosphorylation in mitochondria.
[3]Rasmussen et al., Proc. Nat. Sci., 53, pp:1069–1076 (1965).
[4]Lehninger, Biochem. J., 119, 129–138 (1970).

Any concern with problems of performance and survival in a stressful environment forces the recognition of the complex interplay between the animal and his internal and external environment. This interplay invokes intuitive and learned, involuntary and voluntary responses, designed to maintain a stable equilibrium essential for survival. For lack of better terminology the manifold reactions that constitute the response to a homeostatis displacement have been lumped into a catchall designation of stress. From a biochemical standpoint, using acceleration as a model, stress is interpreted as an increased demand for biological energy under conditions of limited supply and predicated an approach on the premise that common bioenergetic factors were operative in stresses of diverse etiology. Some new biochemical correlates of stress and some of their hormonal control factors have been demonstrated. These have been implicated through in vitro studies of mitochondria into primary energy transducing mechanisms. The studies with $PGB_x$ offer a molecular approach to the channelling of biological energy to pathways that should enhance the tolerance to stress and survival of animals in a crisis period.

In order to further illustrate the present invention and the advantages thereof, the following specific examples are given, it being understood that the same are intended merely as illustrative and in no wise limitative.

EXAMPLE 1—PREPARATION OF $PGB_x$ FROM $PGB_1$ 1.86 g of $PGB_1$ was dissolved in 50 ml ethanol and added to 12 g crushed solid KOH in a 500 ml flask using 50 ml additional alcohol to transfer the $PGB_1$. The mixture was rotated on a reflux apparatus at 70° C. for three hours. One hundred ml of water was added to make the final base concentration 1 N KOH in 50% alcohol and the mixture was refluxed in an oil bath at 74° C. for an additional 19 hours. The reaction mixture was cooled to room temperature. 110 ml isobutanol added and adjusted the pH 3 with the addition of about 75 ml 2.3 N HClO$_4$. The precipitate that formed was allowed to settle, the supernatant decanted and the precipitate washed with $H_2O$ and a small amount of alcohol until white. The precipitate was discarded and the colored supernatant and washing combined with an additional 200 ml $H_2O$, 100 ml of isobutanol and extracted at pH 3 (1). The clear $H_2O$ layer was discarded. The red isobutanol layer was washed twice with 100 ml of water and finally extracted with 250 ml of 0.1 M NaHCO$_3$ freshly prepared (pH 8.5) (2). The isobutanol layer now contained a mixture of inactive and inhibitory components, and the NaHCO$_3$ solution contained most of the active components. 100 ml of isobutanol was added to the separated bicarbonate solution of $PGB_x$, and the pH adjusted to 3 with 27 ml of 1 N HCl (3). The active components were then all extracted into the isobutanol layer which was washed with $H_2O$, dried and flash evaporated to yield 1.35 g of a mixture of active components (4). The isobutanol layer from (2) was washed and dried to yield 0.54 mg of material with 1/6 the activity of (4).

EXAMPLE 2—PREPARATION OF $PGB_x$ FROM DEHYDRO $PGB_1$

Two grams of 13-14 dehydroprostaglandin $B_1$ in 100 ml ethanol was heated with 12 g KOH at 70° C. for 5 hours in a 500 ml flask rotated on a reflux apparatus. 100 ml of water was then added and the mixture heated for an additional 19 hours at 72° C. The KOH was neutralized with $HClO_4$ and the crude $PGB_x$ extracted into isobutanol as indicated in Example 1 and the less polar inactive components removed via $NaHCO_3$ extraction of the more polar active components. The active $PGB_x$ in the $NaHCO_3$ layer was extracted into isobutanol at pH 3, washed free of salts and flash evaporated under nitrogen to dryness at 45° C. The yield of active mixture was 1.14 g (57%).

EXAMPLE 3—PURIFICATION BY CHROMATOGRAPHY ON SILICA GEL

Mixtures of $PGB_x$ components prepared as in Examples 1 and 2 and further purified by chromatography on spherosil XOA-400 packed into two 2.5×42 cm stainless steel columns connected in series using a linear gradient of acetonitrile—0.1 N $NH_4OH$—ethyl acetate mixtures from 14:2:4 to 14:4:0. The effluent monitored by U.V. absorption at 280 nm resolved 16 fractions, nine of which had different levels of activity and different migrations on thin layer chromatography. Of 1.3 g applied to the column, 394 mg were recovered with highest activity (A), 238 mg with 90% of A activity; 215 mg with 50% A activity; 58 mg with 20% A activity and 200 mg with no activity.

Further separation of components was achieved by gel filtration on Sephadex LH20 with methanol using two 2.5×100 cm columns linked in series. 5% of starting material was obtained with activity 9x better than that obtained after silica gel chromatography.

Notes:
*Activity predicated on the reactivation effect of the $PGB_x$ preparation on degenerated mitochondria to form ATP from ADP and Pi in the range of 1 to 4μ g $PGB_x$/reaction.
**Conversion of $PGB_1$ or PGB to $PGB_x$ depends on base ($K^+$ is better than $Na^+$), on the concentration of $OH^-$, on the temperature and on the time of heating. Yields vary with the ratio of prostaglandin to base and with the concentration of prostaglandin in the reaction mixture. It is possible to convert the prostaglandin to a derivative with little or no biological activity but with many of the physical chemical properties of $PGB_x$.

Physical and Chemical Properties of $PGB_x$

[1] The molecular weight of the most active and purest preparations of the $PGB_x$ according to the invention is a polymer which suggests a condensed ring structure of prostaglandin units.

[2] The size of the molecule precluded mass spectroscopy.

[3] NMR data for the $PGB_x$ was remarkable only by the absence of proton definition other than $CH_3$, $CH_2$ and deshielded $CH_2$ groups which varied from the starting material and from any known prostaglandin. The most useful information obtained from NMR was the disappearance of unsaturated protons on the $C_{13}$-$C_{14}$ carbons of $PGB_1$, the probable presence of enolic OH groups and the loss of 6 protons/unit reacting prostaglandin.

Methylation with diazomethane added 6 (O—$CH_3$) groups per molecule, suggesting two enolic OH groups in addition to the four carboxylic acid moieties. Methylation with diazomethane destroyed biological activity.

Figure 4:
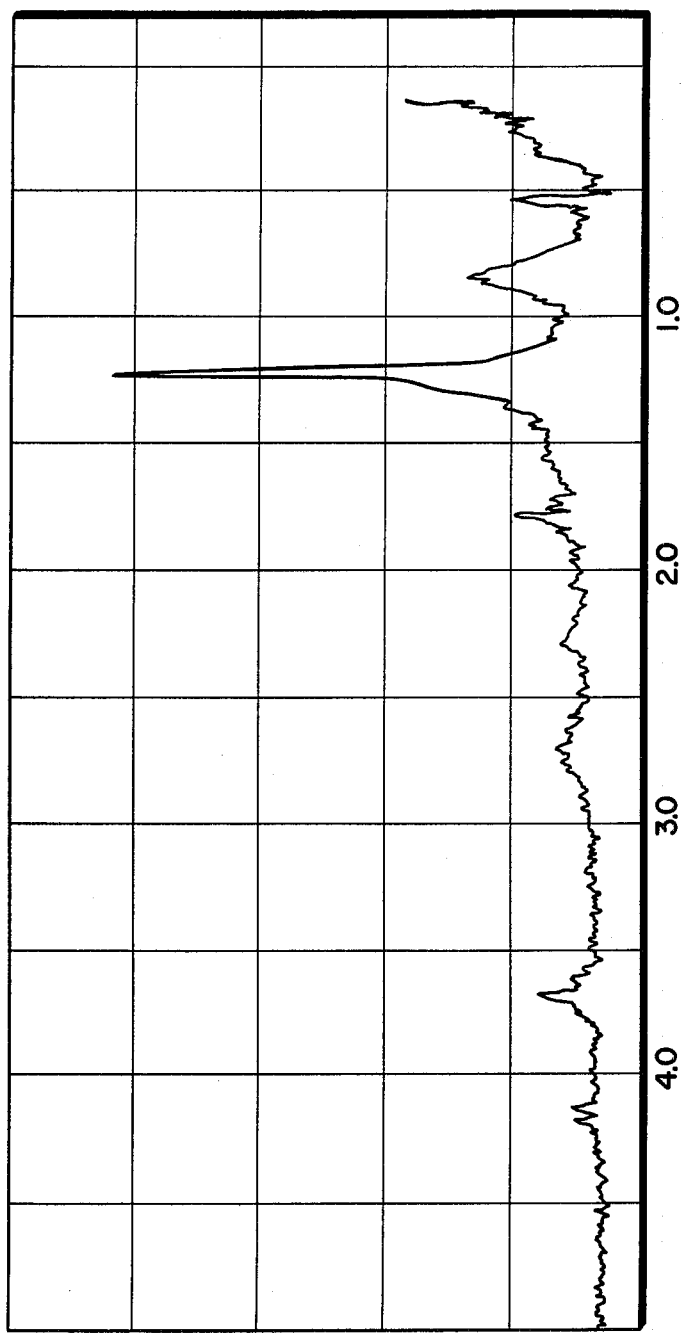
FIG. 4 shows the nuclear magnetic resonance spectrum of $PGB_x$.
Figure 5:
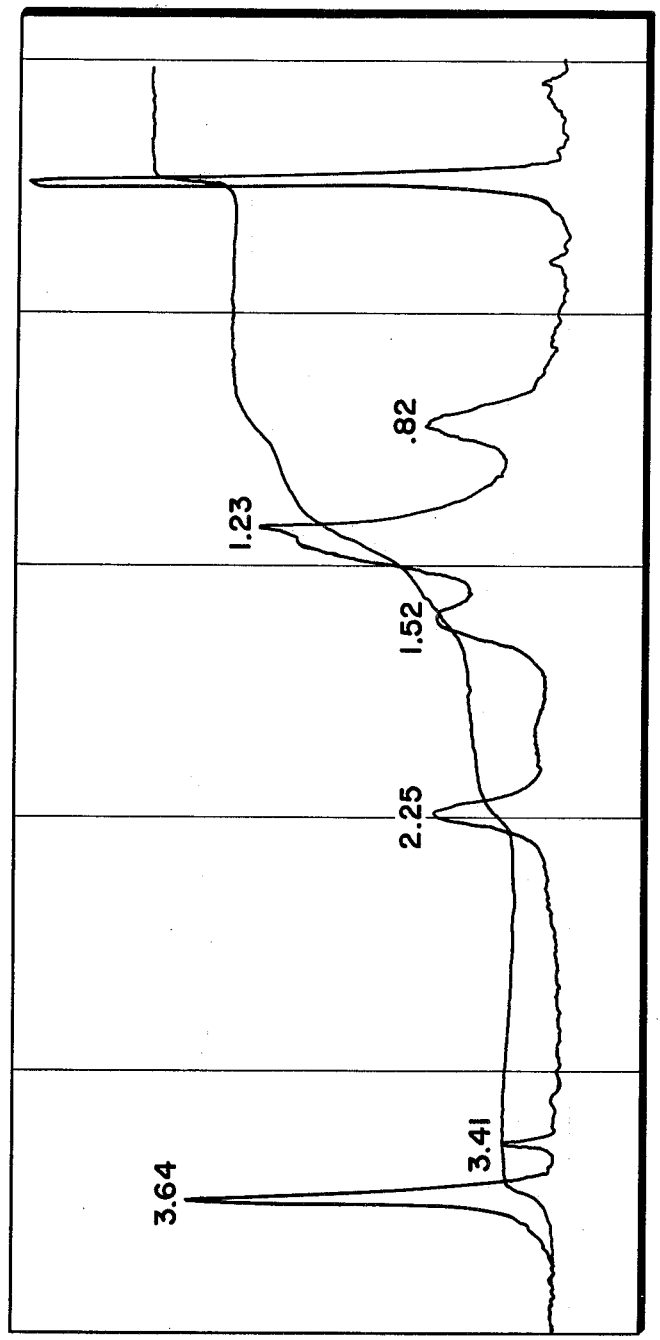
FIG. 5 shows the nuclear magnetic resonance spectrum of methylated $PGB_x$.

In FIGS. 4 and 5, respectively, the NMR data for both $PGB_x$ and methylated $PGB_x$ are shown.

Figure 6:
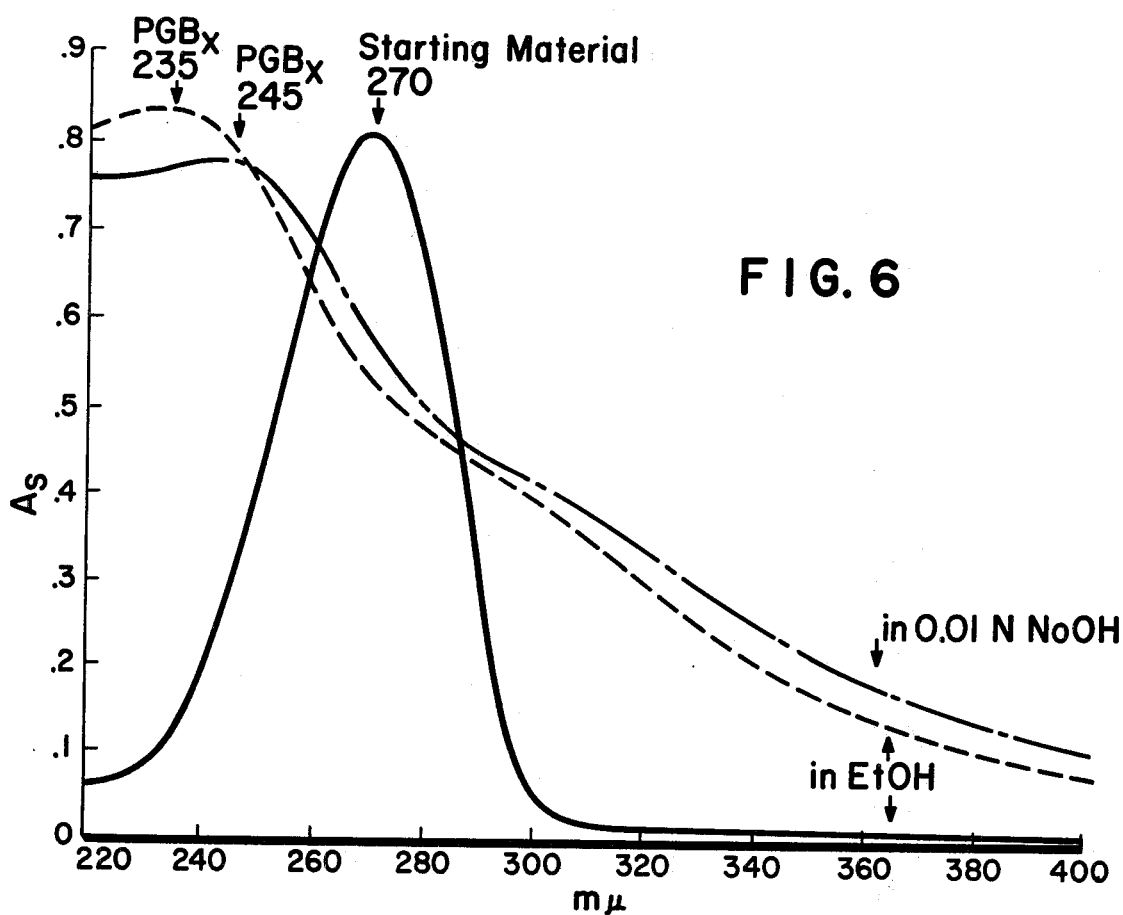
FIG. 6 shows the ultraviolet absorption spectra of dehydro $PGB_1$ starting material and $PGB_x$ in ethanol and 0.01N sodium hydroxide.
Figure 7:
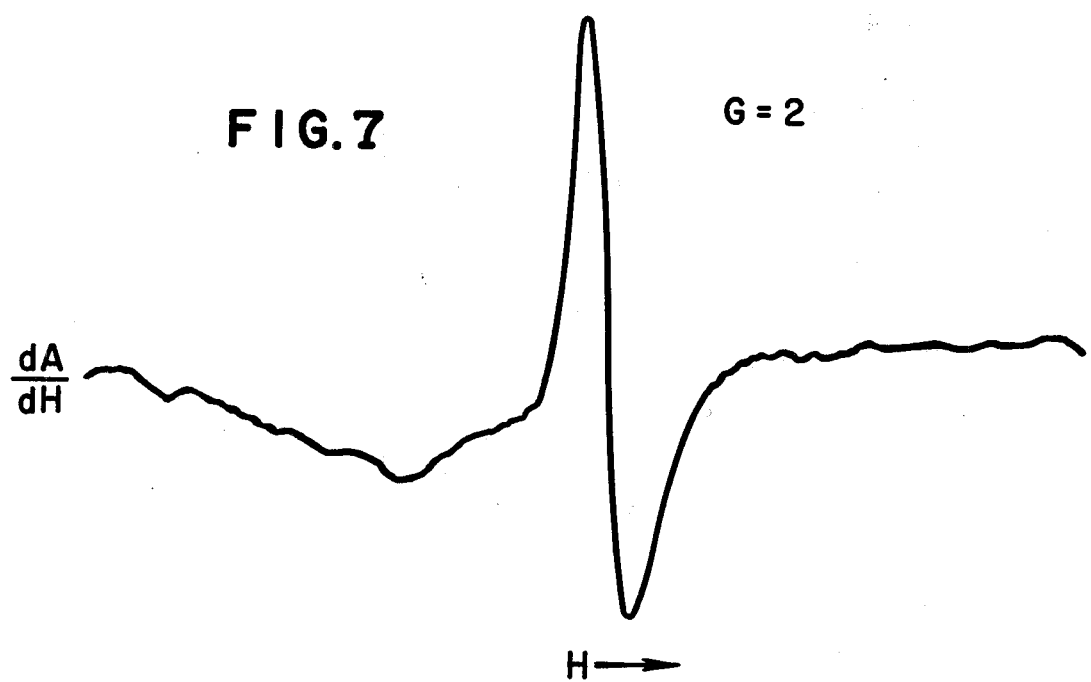
FIG. 7 shows the ESR spectrum of the biologically active $PGB_x$ free radical.
Figure 8:
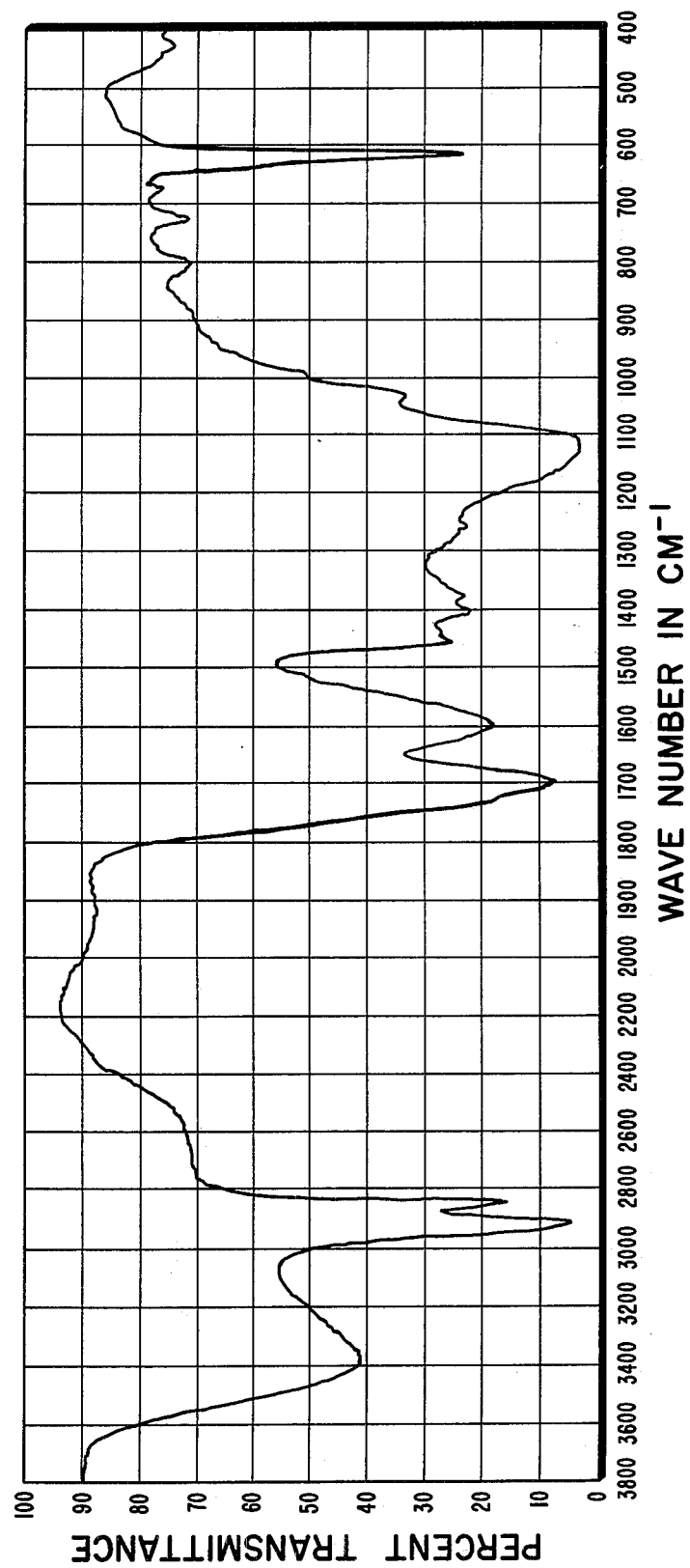
FIG. 8 shows the infrared absorption spectrum of $PGB_x$ ($Na_2SO_4$)
Figure 9:
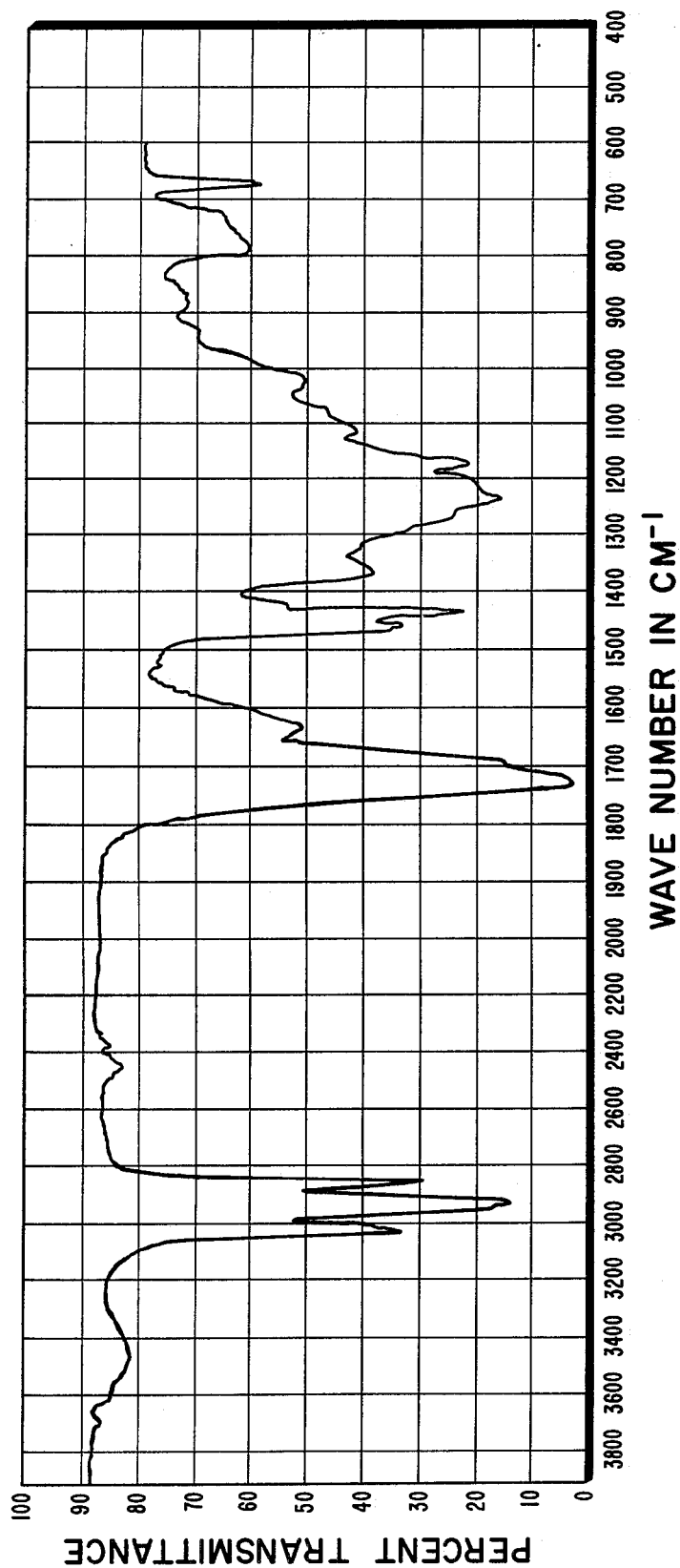
FIG. 9 shows the infrared absorption spectrum of methylated $PGB_x$.

[4] Data from UV and ESR spectrometry showed that the molecule was a conjugated complex of the original $\alpha$-$\beta$ unsaturated cyclopentanone ring that formed a stable free radical in solution that is associated with its unique biological properties. Such data are shown in FIGS. 6 and 7, respectively, with FIG. 6 also reflecting the ultraviolet absorption spectrum of dehydro $PGB_1$.

[5] The infrared absorption spectra of the $PGB_x$ and the methylated $PGB_x$ 8 and 9, respectively.

Figure 10:
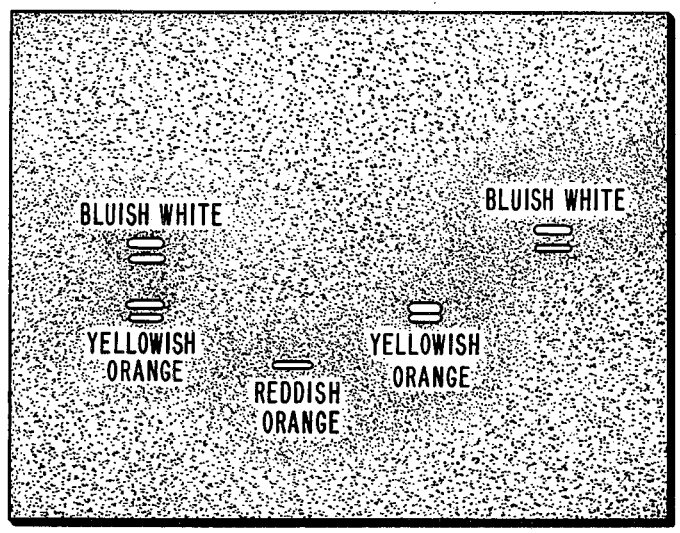
FIG. 10 shows the thin layer chromatograms of the derivatives $PGB_x$.
Figure 11:
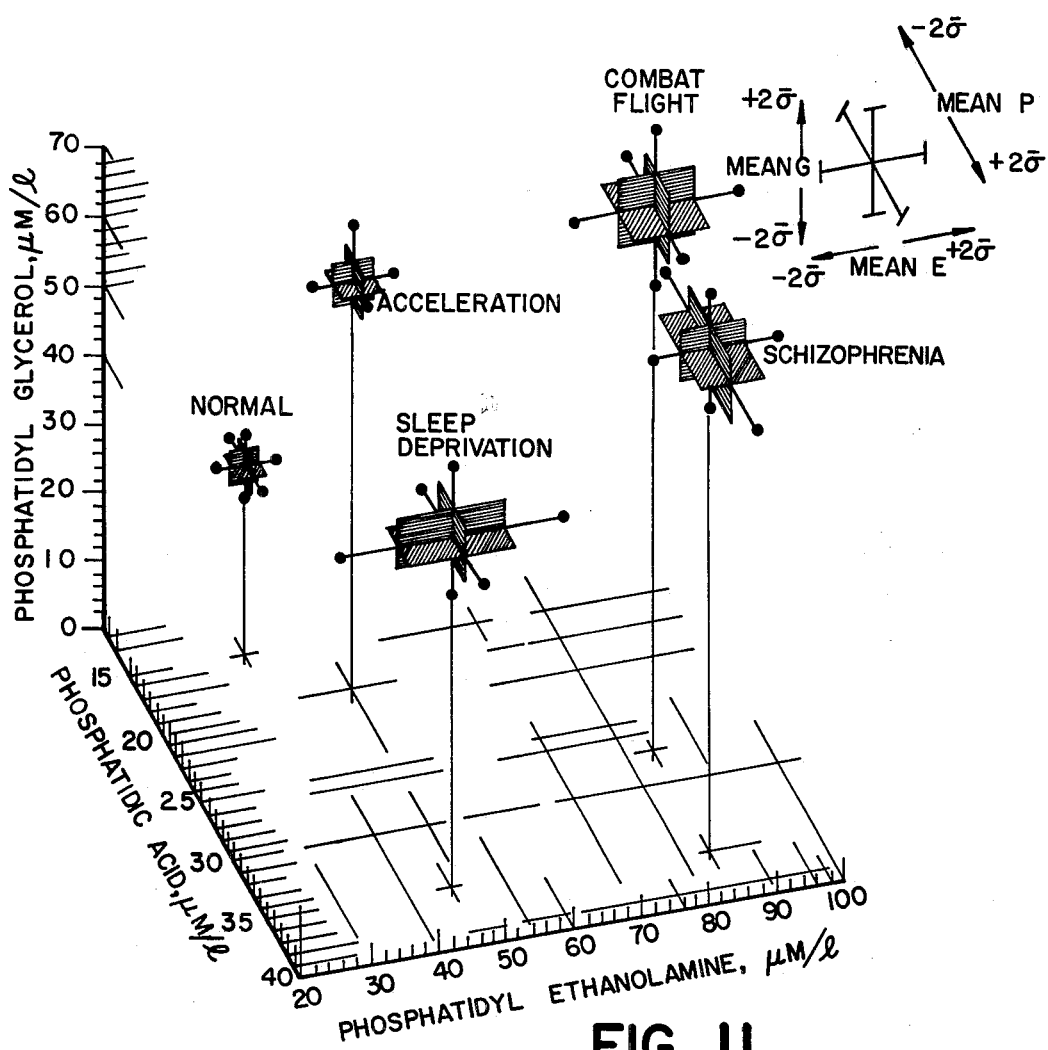
FIG. 11 shows the changes in human plasma phospholipids caused by stress.

[6] In FIG. 10 are shown thin layer chromatograms of the $PGB_x$ derivatives.

[7] Studies with simpler model systems showed that the Ra chain (see [8]) of the prostaglandin could be replaced with a methyl group and the Rb chain could be shortened to an allylic alcohol and retain activity. The initial structural composition necessary for the base catalyzed synthesis of a molecule with the biological activity of $PGB_x$ was an $\alpha,\beta$ unsaturated cyclopentanone ring with an unsaturated chain in allylic position to the ring. Biologically active preparations could be obtained starting with prostaglandin $E_1$, prostaglandin $A_1$, prostaglandin $B_1$, dehydro prostaglandin $B_1$ and from diketoallethralone.

From the foregoing, one of the major distinguishing characteristics of the novel $PGB_x$ derivatives according to the invention resides in its in vitro and in vivo biological property of ability to restore oxidative phosphorylation in degenerated mitochondria that have lost this function. Another distinguishing characteristic of $PGB_x$ comprises its protection and probable reversal of anoxic damage to rat brain [which has been evidenced by creating the equivalent of a stroke or anoxic episode in the rat brain by the known method of tying off the carotid arteries] and thence exerting a protective or restorative effect by the administration of the $PGB_x$. Similarly with respect to the reversal of degenerative changes [coronary infarct] in heart, in vivo, including the rescue of an animal whose heart had gone into fibrillation. The herein reported studies with $PGB_x$ moreover offer a molecular approach to the channelling of biological energy to pathways that should enhance the tolerance to stress and survival of mammalian organisms, both animals and humans, in a crisis period, and thus further provide for the improvement of mammalian performance for conditioned psychological tasks.

While the invention has been described and illustrated with reference to certain preferred embodiments thereof, those skilled in the art will appreciate that various modifications, changes, omissions, and substitutions can be made without departing from the spirit of the invention. It is intended, therefore, that the invention be limited only by the scope of the following claims.

What is claimed is:

1. A method for preparing a class of polymeric prostaglandin derivatives $PGB_x$ comprising the steps of:
    combining a 3.72% solution of $PGB_1$ in ethanol, 24 g KOH per 100 ml of said solution and 100 ml alcohol per 100 ml of said solution to form a first mixture;
    refluxing said first mixture at 70° C. for three hours;
    adding sufficient water to form a second mixture of 1 N KOH in 50% alcohol;
    refluxing said second mixture in an oil bath at 74° C. for 19 hours; and separating the derivatives $PGB_x$ from said second mixture for yielding biologically active components having an in vitro effect on phosphorylation efficiency of aged mitochondria similar to the assay of Table I.

2. A method according to claim 1 wherein said separating step comprises:
adding 220 ml isobutanol per 100 ml of said solution and sufficient 2.3 N $HClO_4$ to said second mixture to form a third mixture of pH 3;
settling said third mixture to form a first precipitate and first supernatent;
combining said first precipitate with water and alcohol to form a second precipitate and a second supernatant;
combining said first and second supernatants with water and 200 ml isobutanol per 100 ml of said solution to form a first isobutanol layer of pH 3 in water;
combining said first isobutanol layer with water and with sufficient 0.1 M $NaHCO_3$ to form a second isobutanol layer on a $NaHCO_3$ solution;
combining said $NaHCO_3$ solution with 200 ml isobutanol per 100 ml of said 3.72% solution and with sufficient 1.0 N HCl to form a third isobutanol layer of pH 3; and
washing said second and third isobutanol layers with water and evaporating to yield the derivatives $PGB_x$.

3. A method according to claim 2 further comprising:
separating said derivatives $PGB_x$ by silica gel chromatography into incremental layers of $PGB_x$ each having a discrete level of biological activity for restoration of phosphorylation in degenerated mitochondria.

4. A method for preparing a class of polymeric stable free-radical prostaglandin derivatives $PGB_x$ comprising the steps of:
combining 3.72% solution of $PGB_1$ in ethanol, 24 g KOH per 100 ml of said solution, and 100 ml alcohol per 100 ml of said solution to form a first reaction mixture;
heating said first reaction mixture at about 70° C. for three hours to form a first product containing the derivatives $PGB_x$;
combining said first product with sufficient water to form a second reaction mixture of 1 N KOH in 50% alcohol;
heating said second reaction mixture at about 74° C. for 19 hours to form a second product containing the derivatives $PGB_x$; and
extracting the derivatives $PGB_x$ from said second product for yielding biologically active components having an in vitro effect on phosphorylation efficiency of aged mitochondria similar to the assay of Table I.

5. A method according to claim 4 wherein said extracting step comprises:
purifying said second product into a water immiscible organic solvent from an acidified reaction.

6. A method according to claim 5 wherein said extracting step further comprises:
forming isobutanol layers in said second product; and washing and drying said layers to form the prostaglandin derivatives $PGB_x$.

7. A method of preparing a class of polymeric prostaglandin derivatives $PGB_x$ comprising the steps of:
combining a 2% solution of 13-14 dehydro-$PGB_1$ in ethanol and 12 g KOH per 100 ml of said solution to form a first mixture;
refluxing said first mixture at 70° C. for five hours;
adding 100 ml water per 100 ml of said solution to form a second mixture;
heating said second mixture at 72° C. for 19 hours; and
separating the derivatives $PGB_x$ from said second mixture for yielding biologically active components having an in vitro effect on phosphorylation efficiency of aged mitochondria similar to the assay of Table I.

8. A method according to claim 7 wherein said separating step comprises:
adding sufficient $HClO_4$ to said second mixture to neutralize said KOH therein;
extracting into a first isobutanol layer the $PGB_x$ formed in said neutralized second mixture;
extracting into a $NaHCO_3$ layer the polar active components of the $PGB_x$ formed in said first isobutanol layer; and
extracting into a second isobutanol layer at pH 3 the more polar active components of the $PGB_x$ formed in said $NaHCO_3$ layer;
washing said second isobutanol layer free of salts and drying under nitrogen.

9. A method according to claim 8 further comprising:
separating said derivatives $PGB_x$ by silica gel chromatography into increments of layers of $PGB_x$ each having a discrete level of biological activity for restoration of phosphorylation in degenerated mitochondria.

10. A method for preparing a class of polymeric stable free-radical prostaglandin derivatives $PGB_x$ comprising the steps of:
combining 2% solution of 13-14 dehydro $PGB_1$ in ethanol and 12 g KOH per 100 ml of said solution to form a first reaction mixture;
heating said first reaction mixture at about 70° C. for five hours to form a first product containing the derivatives $PGB_x$;
combining said first product with 100 ml water per 100 ml of said solution to form a second reaction mixture;
heating said second reaction mixture at about 72° C. for 19 hours to form a second product containing stable free-radical $PGB_x$; and
extracting the derivatives $PGB_x$ from said second product for yielding biologically active components having an in vitro effect on phosphorylation efficiency of aged mitochondria similar to the assay of Table I.

11. A method according to claim 10 wherein said extracting step comprises:
purifying said second product into a water immiscible organic solvent from an acidified reaction.

12. A method according to claim 11 wherein said extracting step further comprises:
forming isobutanol layers in said second product; and washing and drying said layers to form the prostaglandin derivatives $PGB_x$.

* * * * *